(12) United States Patent
Eder et al.

(10) Patent No.: US 9,579,014 B2
(45) Date of Patent: Feb. 28, 2017

(54) OTOSCOPE

(71) Applicant: Heine Optotechnik GmbH & Co KG, Herrsching (DE)

(72) Inventors: Christoph Eder, Munich (DE); Oliver Heine, Herrsching (DE); Roman Raab, Herrsching (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 148 days.

(21) Appl. No.: 14/248,698

(22) Filed: Apr. 9, 2014

(65) Prior Publication Data
US 2014/0336467 A1 Nov. 13, 2014

(30) Foreign Application Priority Data

May 7, 2013 (DE) .......................... 10 2013 208 382

(51) Int. Cl.
*A61B 1/227* (2006.01)
(52) U.S. Cl.
CPC ............ *A61B 1/2275* (2013.01); *A61B 1/227* (2013.01)
(58) Field of Classification Search
CPC ............................. A61B 1/2275; A61B 1/227
USPC .... 600/189, 199–200; 351/59, 223, 207, 57, 351/60; 359/482; 434/303
See application file for complete search history.

(56) References Cited

U.S. PATENT DOCUMENTS

| | | | | |
|---|---|---|---|---|
| 631,227 A | * | 8/1899 | Peppard ................ | G02B 23/18 2/15 |
| 1,515,771 A | * | 11/1924 | Greenwald .......... | A61B 1/2275 600/200 |
| 2,039,546 A | * | 5/1936 | McGerry ............. | A61B 1/2275 600/200 |
| 3,698,387 A | | 10/1972 | Moore et al. | |
| 3,728,998 A | * | 4/1973 | Heine .................... | A61B 1/227 385/117 |

(Continued)

FOREIGN PATENT DOCUMENTS

DE 2029892 A1 4/1971
DE 2203357 A1 8/1972
(Continued)

OTHER PUBLICATIONS

Sauer, J: Cineroid EVF-4L—Video-Sucher fuer DSLR-Kameras, Sep. 12, 2010. URL: http://www.colorfoto.de/news/cineroid-evf-4l-video-sucher-fuer-kameras-1038714.html.

*Primary Examiner* — Todd E Manahan
*Assistant Examiner* — Marcela I Shirsat
(74) *Attorney, Agent, or Firm* — Bachman & LaPointe, PC

(57) ABSTRACT

The otoscope comprises a head portion (11) including a through-hole (24) extending continuously from a proximal end to a distal end along a viewing path and a speculum receptacle (14) tapering towards the distal end and surrounding the through-hole (24), wherein a speculum (50) is attachable to the speculum receptacle (14). Lens means (26) including at least one lens (36) is configured to be movable from a viewing position, in which the lens (36) is arranged in the viewing path, to a clearance position, in which the lens (36) is arranged outside the viewing path. In the viewing position of the lens means (26) the lens (36) is arranged inside the through-hole (24) far enough for the distance between the lens (36) and the distal end (52) of an attached speculum (50) to be smaller than the focal length (F) of the lens (36).

17 Claims, 3 Drawing Sheets

(56) References Cited

U.S. PATENT DOCUMENTS

| | | | | | |
|---|---|---|---|---|---|
| 3,934,578 | A | * | 1/1976 | Heine | A61B 1/227 313/318.01 |
| 4,366,811 | A | * | 1/1983 | Riester | A61B 1/227 600/200 |
| 4,643,171 | A | * | 2/1987 | Riester | A61B 1/07 600/200 |
| 6,217,512 | B1 | * | 4/2001 | Salo | A61B 1/0676 600/135 |
| 6,264,325 | B1 | * | 7/2001 | Peressini | G02C 5/005 351/41 |
| 2008/0051637 | A1 | * | 2/2008 | Andreassen | A61B 1/227 600/200 |
| 2013/0178707 | A1 | | 7/2013 | Kwong | |

FOREIGN PATENT DOCUMENTS

| | | |
|---|---|---|
| DE | 19815927 A1 | 10/1999 |
| DE | 202008005144 U1 | 6/2008 |
| WO | 2012035351 A1 | 3/2012 |

\* cited by examiner

OTOSCOPE

BACKGROUND OF THE INVENTION

The present invention relates to an otoscope.

DE 2 029 892 A discloses an otoscope having a head portion and a speculum portion adjoining the head portion with a through-hole extending through the head and speculum portions. At the proximal end of the head portion, i.e. at the end which during an ear examination faces towards the person performing the examination, the through-hole is closed by a lens arranged in a lens frame guided horizontally and perpendicularly to the central axis of the through-hole by means of a dovetail guide at the proximal end of the head portion. If it is necessary to introduce an instrument through the through-hole into a patient's ear, the lens frame with the lens is removed from the guide by a lateral sliding movement in order to enable introduction of an instrument through the through-hole from the proximal side into the distally located ear.

A different solution is disclosed in DE 2 203 357 A. In the otoscope known from this citation, the lens is supported in a lens frame arranged at the proximal end side of head portion and being pivotable about an axis which is parallel to the central axis of the through-hole. The lens frame may be pivoted from a viewing position, in which the lens is aligned with the through-hole, into a clearance position, in which the proximal end of the through-hole is cleared to enable an instrument to be introduced through the through-hole into the ear.

Thus the two known otoscopes described above have in common that the lens is arranged such that it closes the proximal end of the through-hole, which means that it is not arranged inside the through-hole.

DE 20 2008 005 144 U1 discloses an otoscope comprising a speculum receptacle surrounding the through-hole at the distal end of the head portion, wherein a speculum made of plastic material may be attached to the speculum receptacle for being introduced into a patient's ear during an examination. After the examination the plastic speculum is ejected and replaced by a new one in order to avoid cross contamination.

In known otoscopes with the above-mentioned configuration, i.e. having a lens which closes the proximal end of the through-hole, the magnification is normally not higher than three-fold. The magnification of magnifying glass lenses is defined by the reference seeing distance (the least distance of distinct vision) and the focal length of the magnifying glass lens. The highest magnification is located at the focal point of the magnifying glass lens. For otoscopes a reference seeing distance of about 250 mm is considered to be a value that enables a comfortable viewing experience. After attachment of a plastic speculum the overall installation length of an otoscope is normally about 65 mm. Together with a distance of 15 mm between the plane of examination and the speculum tip, the distance between the magnifying glass lens and the object being examined is about 80 mm. Use of a magnifying glass lens having a focal length of 85 mm in these geometries will result in a magnification of about 2.95 times. Thus the magnification of an otoscope is limited by the installation length of the device and the resulting possible focal length of the lens. If a higher magnification is to be realized (i.e. a lens with shorter focal length is to be used), the range of sharp focus will be located nearer to the lens. Merely using a different lens in a given otoscope design would move the range of sharp focus into the attached speculum, which would render a sharp representation of the object to be examined impossible.

The object underlying the invention is to create an otoscope by means of simple design which enables to view the area to be examined in a patient's ear with high magnifications and excellent sharpness.

SUMMARY OF THE INVENTION

The foregoing object is achieved by providing an otoscope according to the invention as set forth hereinbelow.

In contrast to the prior art as described above, the lens of the otoscope according to the present invention is not arranged at the proximal end side of the head portion to close the proximal end of the through-hole, but in the viewing position of a lens means according to the invention the lens is arranged inside the through-hole in such a way that the distance between the lens and the distal end of an attached speculum is smaller than the focal length of the lens. Due to the fact that the lens is arranged within the through-hole, i.e. at a distance from the proximal end of the head portion or of the through-hole, it is possible to use lenses having higher magnification factors.

In a preferred embodiment, the lens means comprises a pivotable element having a cavity and being supported at the proximal end of the head portion to be pivotable about a pivot axis extending perpendicularly to the central axis of the through-hole, wherein the lens is arranged in the pivotable element. To be more precise, the pivot axis perpendicularly intersects a plane in which the central axis of the through-hole is located. The central axis of a battery handle of an otoscope may also be located in this plane.

In the viewing position the pivotable element preferably closes the proximal end of the through-hole in a gas-tight manner. This enables to apply increased air pressure to the examination area, for example, in order to examine movement of the tympanic membrane. Preferably, a port for a source of pressurized gas is provided at the head housing to accomplish build-up of pressure, wherein the port is connected to the through-hole. The source of pressurized gas may, for example, be formed by bellows.

The magnification of the lens may be at least 4-fold, wherein the lens is preferably be configured to be arranged such that its focal length is larger than its distance to the distal end of the attached speculum by about 2 to 20 mm, preferably 5 to 15 mm.

Advantageously the pivotable element is fixable in the viewing position and/or in the clearance position by fastening means. This is, for example, accomplished by locking means which secure the pivotable element in the viewing position and/or in the clearance position in order to prevent unintentional lowering of the pivotable element on the one hand and, on the other hand, to enable air-tight closure of the proximal end of the head housing in the viewing position.

A detachable snap-on connection may be used as the locking means. However, it is preferable to make use of magnetic means which retain the cover in the viewing position and/or in the clearance position. In this case only minimal strain is exerted on the mechanics, and a very high number of pivoting procedures may be performed without reducing its retaining force and precision due to wearing out, as it may happen in the case of snap-on connections.

The pivoting movement may be aided by means of a spring mechanism which provides active support for the movement, wherein the cover is lifted up automatically after it has been pivoted up to a small extent. In the clearance position the pivotable element may be retained by the spring force.

Preferably a contact surface for the fingers of the person performing the examination may be integrated in the surface or the margin of the pivotable element to allow for resting of the fingers during an examination or a treatment.

The magnifying glass lens may be configured as a single piece. For improved optical quality, especially in the case of higher magnifications, the lens may be configured as an aspheric or achromatic lens which allows achieving an improved correction of imaging aberrations.

If adjustable magnification is required, the magnifying lens may be configured as a two-lens system with a variable air space between the two lenses. In this case advantageously one lens is fixed at the proximal end of the head portion and the other lens is axially displaced within the pivotable element in order to vary the magnification factor. Typically a biconvex lens or a plano-convex lens is combined with a biconcave or plano-concave lens.

In a preferred embodiment the pivotable element comprises an annular collar portion supported at the head portion to be pivotable and abutting on the proximal end of the head portion in the viewing position of the pivotable element. A hollow support portion is connected to the collar portion and extends into the through-hole in the viewing position of the pivotable element, wherein the lens is arranged at the free end of the hollow support portion.

The proximal end of the cavity of the pivotable element may be closed by a protective glass or an optical element.

BRIEF DESCRIPTION OF THE DRAWINGS

Hereinafter exemplary embodiments of the invention will be described in more detail with reference to the accompanying drawings, in which.

DETAILED DESCRIPTION

Figure 1:
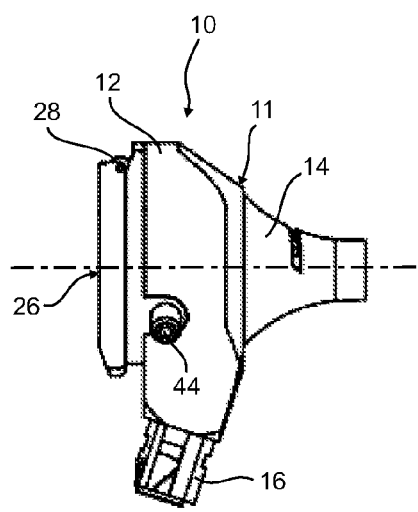
FIG. 1 shows a side view of an otoscope head with a pivotable element in a viewing position.

The otoscope head 10 shown in FIGS. 1 to 6 has a head portion 11 comprising a head housing 12 in which an inner cone 18 is arranged which tapers from a proximal end to a distal end and has a distal aperture 17. At its proximal end the inner cone 18 has an outer collar 23 adjoining the proximal end side of the head housing 12. An outer cone 19 forming a speculum receptacle 14 is secured to the distal end of the head housing 12 and coaxially surrounds the inner cone 18 with a distance therebetween. The distal ends of the inner cone 18 and of the outer cone 19 are flush with one another.

The head housing 12 has a downwardly extending protrusion 20, wherein a plug connector 16 adapted to attach the head portion 11 to a battery handle (not shown) is provided at the bottom end of the protrusion 20. A through-hole 22 extends through the plug connector 16 and the protrusion 20 and opens into the space between the inner cone 18 and the outer cone 19. An illuminant, for example an LED or a light bulb, which is supplied with electric power from the battery handle, is arranged in the through-hole 22. Light-transmitting optical fibers (not shown) are arranged in the space between the inner cone 18 and the outer cone 19 and terminate at the distal end of the two cones.

Figure 2:
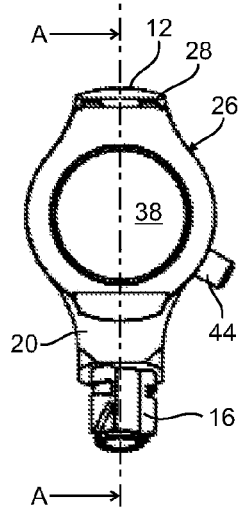
FIG. 2 shows a proximal view of the otoscope head of FIG. 1.
Figure 3:
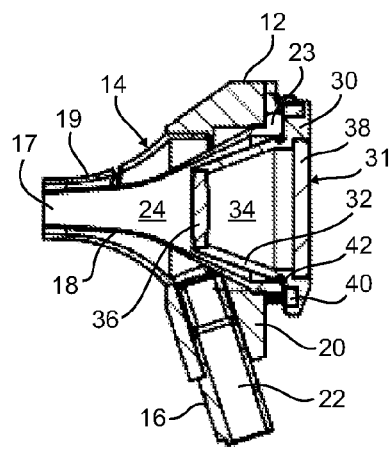
FIG. 3 shows the cross section A-A of FIG. 2.

The inner cone 18 surrounds a through-hole 24 tapering towards the distal end, wherein a lens means 26 engages in the through-hole 24 when the lens means 26 is in the viewing position shown in FIGS. 1 to 3. The lens means 26 includes a pivotable element 31 comprising an outer collar 30 surrounding a cavity 34, which in the viewing position shown in FIG. 3 abuts on the outer collar 23 of the inner cone 18. A support portion 32 surrounding the cavity 34 extends from the outer collar 30 and conically tapers into the through-hole 24, wherein a lens 36 distally closing the cavity 34 is arranged at the free end of the support portion 32. At its proximal end the cavity 34 is closed by a protective glass 38.

The pivotable element 31 is articulated at the—in the figures—upper portion of its outer collar 30, i.e. on the opposite side of the protrusion 20, by means of a hinge 28 at the outer collar 23 of the inner cone 18 such that the pivotable element 31 is pivotable about a pivot axis extending perpendicularly to the central axis of the through-hole 24 when the otoscope head 10 is viewed from the top. To be precise, the pivot axis perpendicularly intersects a plane in which the central axis of the through-hole 24 is located. Normally the central axis of the protrusion 20 and of the through-hole 22 is also located in this plane.

An annular seal 42 is arranged at the transition between the outer collar 30 and the support portion 32 of the pivotable element 31 and seals against the inner proximal edge of the inner cone 18 when the pivotable element 31 is in the viewing position shown in FIG. 3. It goes without saying that a corresponding annular seal may also be provided at the inner cone 18 and seal against the pivotable element.

A magnet 40 facing towards the proximal end of the inner cone 18 is arranged in the bottom portion of the outer collar 30 of the pivotable element 31 and in the position shown in FIG. 3 abuts on the proximal end side of the outer collar 23. The pivotable element 31 is retained in the viewing position due to the magnetic force between the inner cone 18 and the magnet 40. Corresponding magnets may also be distributed at the circumference of the outer collar 30.

When the pivotable element 31 is in the above viewing position, the person performing the examination is able to view an area in the ear of a person to be examined via the viewing path extending through the through-hole 24 and the attached speculum 50 through the lens 36.

Figure 4:
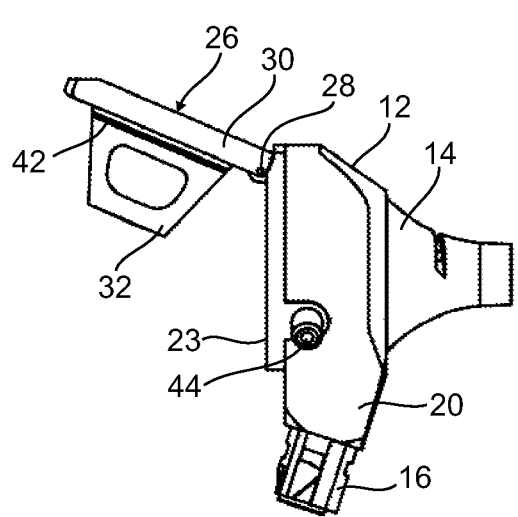
FIG. 4 shows a side view of the otoscope head of FIG. 1 with the pivotable element folded out.
Figure 5:
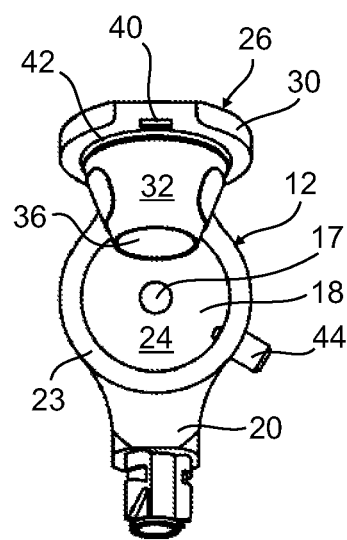
FIG. 5 shows a proximal view of the otoscope head of FIG. 1 with the pivotable element folded out.

The pivotable element 31 may be pivoted about the pivot axis upwardly from the viewing position into the clearance position shown in FIGS. 4 and 5, for example, in cases where it is necessary to introduce an instrument through the through-hole 24 into the ear of a patient.

A port 44 extending through a recess in the head housing 12 is arranged at the outside of the inner cone 18 and opens into the through-hole. Bellows may be connected to the port 44 in cases where pressure is to be applied to the ear during an examination. In this case the pivotable element 31 is in the viewing position.

Figure 6:
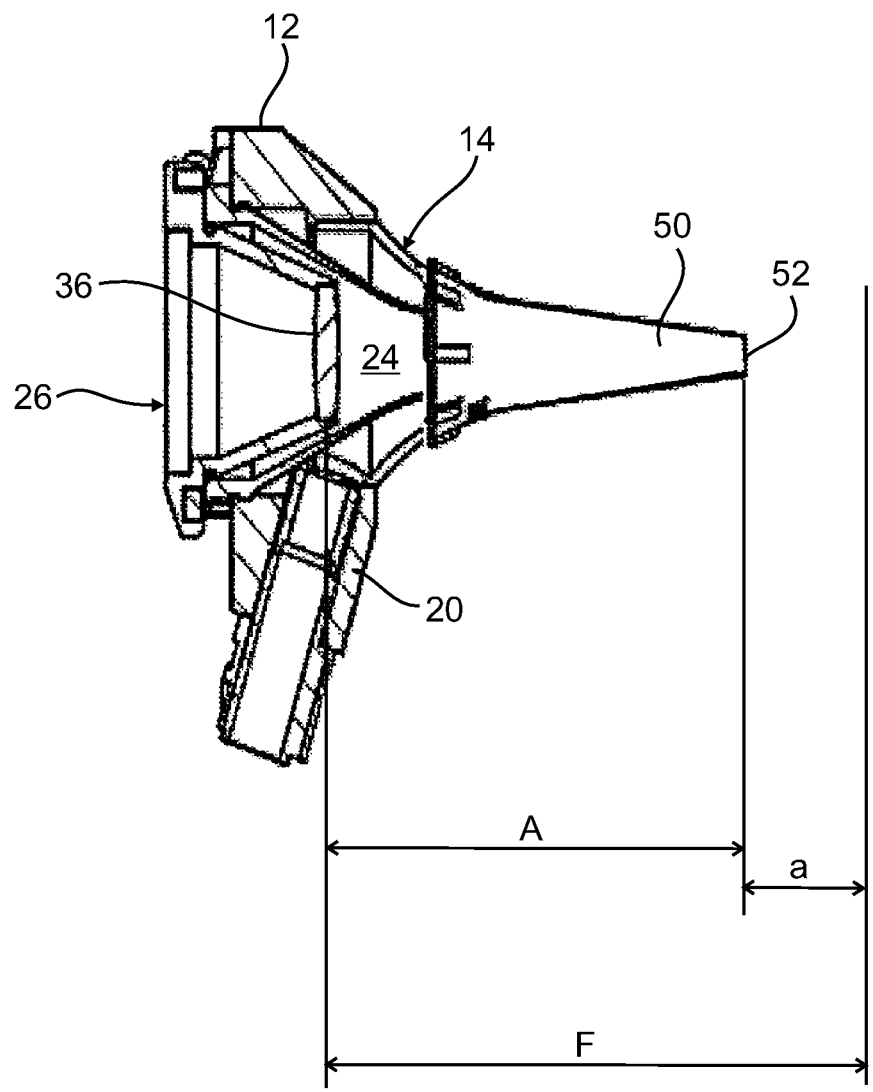
FIG. 6 shows a longitudinal section of the otoscope head of FIG. 1 with attached speculum.

As shown in FIG. 6, the lens 36 is configured and arranged such that the distance between the lens 36 and the area to be examined is larger by an amount a than the distance between the lens 36 and the distal end 52 of the attached speculum 50.

During an examination the distance between the lens 36 and the area to be examined should match the focal length F of the lens 36 in order to enable the sharpest possible representation of the area to be examined. The distance a between the distal end 52 of the attached speculum 50 and the area to be examined is preferably 2 to 20 mm, more preferably 5 to 15 mm. Thus the lens 36 is arranged at a distance A=F−a from the distal end 52 of the attached speculum. Preferably the lens has a magnification factor of at least 4.

The invention claimed is:

1. An otoscope comprising:
   a head portion including a through-hole extending continuously from a proximal end to a distal end along a viewing path having a conically tapered portion, and a speculum receptacle tapering towards said distal end and surrounding said through-hole, wherein a speculum is attachable to said speculum receptacle; and
   lens means including at least one lens and being configured to be movable from a viewing position, in which said lens is arranged in said conically tapered portion of said viewing path, to a clearance position, in which said lens is arranged outside said viewing path;
   wherein in said viewing position of said lens means said lens is arranged inside said through-hole far enough for a distance between said lens and a distal end of an attached speculum to be smaller than a focal length of said lens, and wherein said lens means comprises a pivotable element supported at said proximal end of said head portion to be pivotable about a pivot axis extending perpendicularly to a central axis of said through-hole, wherein the pivotable element comprises:
   an annular collar portion supported at said head portion to be pivotable and abutting on said proximal end of said head portion in said viewing position of said pivotable element, and
   a hollow support portion connected to said collar portion extending into said through-hole in said viewing position of said pivotable element, wherein said lens is arranged at a free end of said hollow support portion.

2. The otoscope according to claim 1, wherein in said viewing position said pivotable element closes said proximal end of said through-hole in a gas-tight manner.

3. The otoscope according to claim 1, wherein a port for a source of pressurized gas is provided at said head portion, wherein said port is connected to said through-hole.

4. The otoscope according to claim 1, wherein a magnification of said lens is at least 4-fold.

5. The otoscope according to claim 1, wherein said lens is configured and arranged such that a focal length thereof is larger than a distance between said lens and said distal end of said attached speculum by 2 to 20 mm.

6. The otoscope according to claim 1, wherein said lens is configured and arranged such that a focal length thereof is larger than a distance between said lens and said distal end of said attached speculum by 5 to 15 mm.

7. The otoscope according to claim 1, wherein said pivotable element is fixable to said head portion in said viewing position by fastening means.

8. The otoscope according to claim 7, wherein said pivotable element is fixable to said head portion in said viewing position by magnetic means.

9. The otoscope according to claim 1, wherein said pivotable element is fixable to said head portion in said clearance position by fastening means.

10. The otoscope according to claim 1, wherein a proximal end of a cavity of said pivotable element is closed by a protective glass or an optical element.

11. An otoscope comprising:
    a head portion including a through-hole extending continuously from a proximal end to a distal end along a viewing path having a conically tapered portion, and a speculum receptacle tapering towards said distal end and surrounding said through-hole, wherein a speculum is attachable to said speculum receptacle; and
    lens means including at least one lens and being configured to be movable from a viewing position, in which said lens is arranged in said conically tapered portion of said viewing path, to a clearance position, in which said lens is arranged outside said viewing path;
    wherein in said viewing position of said lens means said lens is arranged inside said through-hole far enough for a distance between said lens and a distal end of an attached speculum to be smaller than a focal length of said lens,
    wherein a magnification of said lens is at least 4-fold, and
    wherein said lens is configured and arranged such that a focal length thereof is larger than a distance between said lens and said distal end of said attached speculum by 2 to 20 mm.

12. An otoscope comprising:
    a head portion including a through-hole extending continuously from a proximal end to a distal end along a viewing path having a conically tapered portion, and a speculum receptacle tapering towards said distal end and surrounding said through-hole, wherein a speculum is attachable to said speculum receptacle; and
    lens means including at least one lens and being configured to be movable from a viewing position, in which said lens is arranged in said conically tapered portion of said viewing path, to a clearance position, in which said lens is arranged outside said viewing path;
    wherein in said viewing position of said lens means said lens is arranged inside said through-hole far enough for a distance between said lens and a distal end of an attached speculum to be smaller than a focal length of said lens,
    wherein a magnification of said lens is at least 4-fold, and
    wherein said lens is configured and arranged such that a focal length thereof is larger than a distance between said lens and said distal end of said attached speculum by 5 to 15 mm.

13. An otoscope comprising:
    a head portion including a through-hole extending continuously from a proximal end to a distal end along a viewing path having a conically tapered portion, and a speculum receptacle tapering towards said distal end and surrounding said through-hole, wherein a speculum is attached to said speculum receptacle; and
    lens means including at least one lens and being configured to be movable from a viewing position, in which said lens is arranged in said conically tapered portion of said viewing path, to a clearance position, in which said lens is arranged outside said viewing path;
    wherein in said viewing position of said lens means said lens is arranged inside said through-hole far enough for a distance between said lens and a distal end of said attached speculum to be smaller than a focal length of said lens, wherein said lens means comprises a pivotable element having a cavity and being supported at said proximal end of said head portion to be pivotable about a pivot axis extending perpendicularly to a central axis of said through-hole, wherein said lens is arranged in said pivotable element.

14. The otoscope according to claim 13, wherein a magnification of said lens is at least 4-fold.

15. The otoscope according to claim 13, wherein said lens is configured and arranged such that a focal length thereof is larger than a distance between said lens and said distal end of said attached speculum by 2 to 20 mm.

16. The otoscope according to claim 13, wherein said lens is configured and arranged such that a focal length thereof is larger than a distance between said lens and said distal end of said attached speculum by 5 to 15 mm.

17. The otoscope according to claim 15, wherein a magnification of said lens is at least 4-fold.

* * * * *